United States Patent [19]

Iwayama et al.

[11] Patent Number: 4,861,928

[45] Date of Patent: Aug. 29, 1989

[54] PROCESS FOR THE ISOMERIZATION OF DICHLOROTOLUENE

[75] Inventors: Kazuyoshi Iwayama; Yasuhiro Magatani, both of Aichi; Kuniyuki Tada, Kanagawa, all of Japan

[73] Assignee: Toray Industries, Inc., Tokyo, Japan

[21] Appl. No.: 152,406

[22] Filed: Feb. 4, 1988

[30] Foreign Application Priority Data

Feb. 9, 1987 [JP] Japan .................................. 62-26386

[51] Int. Cl.$^4$ ........................ C07C 17/00; C07C 25/02
[52] U.S. Cl. .................................................. 570/202
[58] Field of Search ......................................... 570/202

[56] References Cited

FOREIGN PATENT DOCUMENTS 3334674 4/1985 Fed. Rep. of Germany ...... 570/202
144330 8/1983 Japan .................................. 570/202

Primary Examiner—Howard T. Mars
Attorney, Agent, or Firm—Austin R. Miller

[57] ABSTRACT

By using a catalyst containing an acid type zeolite and at least one component of metal selected from the group consisting of rhenium, nickel and silver and isomerizing a mixture of the isomers of dichlorotoluene in the presence of hydrogen, the concentration of at least one or more components of the isomers of dichlorotoluene can be increased. According to this method, there is provided a process for isomerization of DCT which exhibits a high isomerization capacity not degraded with reaction time.

7 Claims, 3 Drawing Sheets

———●——— EXAMPLE 2
———○——— COMPARATIVE EXAMPLE 1

—●— EXAMPLE 4
—○— COMPARATIVE EXAMPLE 3

PROCESS FOR THE ISOMERIZATION OF DICHLOROTOLUENE

BACKGROUND OF THE INVENTION

1. Field of the Invention

This invention relates to a process for the isomerization of dichlorotoluene (hereinafter referred to as "DCT").

2. Description of the Prior Art

In general, DCT is obtained by dichlorination of toluene. But, this reaction is a strongly orientated reaction, and the types of isomers obtained and the production ratios of isomers are: 2,4-DCT, 20-30%; 2,5-DCT, 25-55%; 2,6-DCT 5-25%; 2,3-DCT, 8-12% and 3,4-DCT, 5-12%. By this reaction, 3,5-DCT is not obtainable, and so when it is desired to obtain 3,5-DCT, it is necessary to isomerize DCT.

Each DCT isomer or 3,5-DCT produced by isomerization has to be separated when it is intended to be used independently. These isomers have very similar boiling points to one another and are not separable by conventional distillation, and the separation is achieved by, for example, the adsorption separation method or a combination of adsorption separation and distillation, as disclosed in U.S. Pat. No. 4,254,062.

After the intended DCT isomer has been separated, it is economically important that the remaining DCT isomers have the concentration of the subsequently intended isomer increased by the isomerization reaction. Such isomer is then separated, and this cycle is repeated.

As a method for such isomerization reaction, there have been disclosed, in Japanese Examined Patent Publication No. 144330/1983 and West Germany Unexamined Patent Specification Nos. 3,334,673 and 3,334,674, methods which are mordenite zeolite. But, such method is not sufficient in the capacity of isomerizing DCT and involves the difficulty that the isomerization capacity tends to decrease with the reaction time.

In order to effect the isomerization of DCT on an industrial scale, it is necessary to maintain the catalyst activity for a long term. According to the methods of isomerization reaction heretofore known, the catalyst is degraded greatly with reaction time, and in case a higher isomerization ratio is desired, the degradation with reaction time further increases greatly. Thus, it was required to lower the isomerization ratio in order to suppress the speed of degradation. Nevertheless, the degradation occurred. Thus, such methods were not preferable for industrial isomerization.

SUMMARY OF THE INVENTION

One object of the present invention is to provide a process for the isomerization of DCT which shows a high isomerization capacity.

Another object of the invention is to provide a process for isomerization of DCT which has an isomerization capacity not degraded with reaction time.

It is a further object of the present invention to provide a process for the isomerization of DCT which allows continuous operation and is efficient and industrially distinguished.

Other and further objects, features, and advantages of the invention will appear more fully from the following description.

These objects are attained by a process for isomerization of DCT comprising contacting a mixture of DCT isomers with a catalyst containing an acid type zeolite and at least one metal selected from the group consisting of rhenium, nickel, and silver such contact being performed in the presence of hydrogen.

DESCRIPTION OF THE PREFERRED EMBODIMENTS

Figure 1:
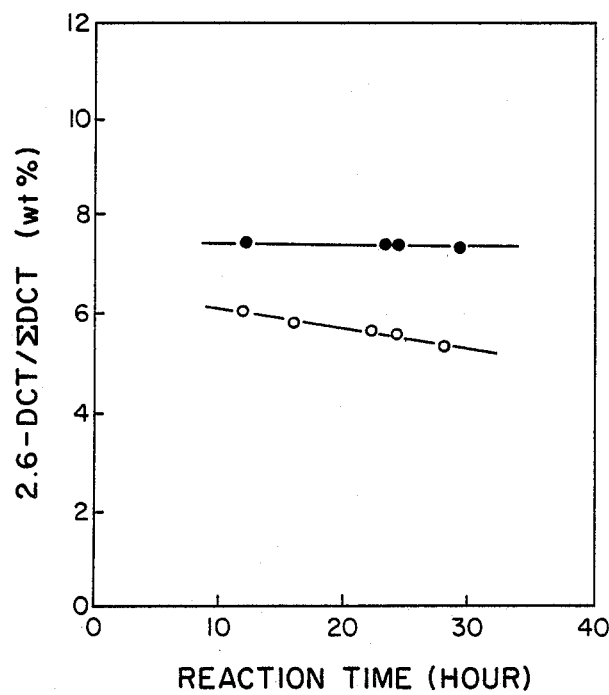
FIG. 1 is a graph showing the relation between the concentration of 2,6-DCT and the reaction time, with respect to the result of Example 2 and Comparative Example 1 of the specification.

For the acid type zeolite used in the practice of the invention, any zeolites are usable, provided they are adapted to isomerize the mixture of DCT isomers. Of these, particularly preferred are beta zeolite, mordenite zeolite, and pentasil zeolite.

A synthetic method of indicating beta zeolite is disclosed, for example, in U.S. Pat. No. 3,308,069. The most conventional method to indicate the beta zeolite is the X-ray diffraction pattern. The characteristic X-ray diffraction of the beta zeolite is as shown in Table 1.

TABLE 1

| X-ray Diffraction Pattern | |
|---|---|
| Interplanar Spacing d(A) | Strength* |
| 11.7 ± 0.2 | M |
| 4.18 ± 0.08 | M |
| 3.98 ± 0.08 | VS |
| 3.53 ± 0.08 | W |
| 3.35 ± 0.08 | M |
| 3.32 ± 0.08 | M |
| 3.08 ± 0.08 | W |
| 2.69 ± 0.08 | W |

*VS represents very strong; M medium strength; and W weak.

A synthetic method of indicating mordenite zeolite is disclosed for example, in Japanese Examined Patent Publication No. 46677/1972 and European Patent No. 57016.

The most conventional method to indicate the mordenite zeolite is the X-ray diffraction pattern. The characteristics X-ray diffraction pattern of the mordenite zeolite is as shown in Table 2.

TABLE 2

| X-ray Diffraction Pattern | |
|---|---|
| Interplanar Spacing d(Å) | Strength |
| 13.6 ± 0.2 | M |
| 10.2 ± 0.2 | W |
| 9.0 ± 0.2 | S |
| 6.56 ± 0.1 | S |
| 6.40 ± 0.1 | M |
| 6.05 ± 0.1 | W |
| 5.80 ± 0.1 | M |
| 4.52 ± 0.08 | M |
| 3.99 ± 0.08 | S |
| 3.83 ± 0.08 | W |
| 3.76 ± 0.08 | W |
| 3.53 ± 0.05 | W |
| 3.46 ± 0.05 | VS |
| 3.38 ± 0.05 | S |
| 3.28 ± 0.05 | W |
| 3.20 ± 0.05 | S |

TABLE 2-continued

| X-ray Diffraction Pattern | |
|---|---|
| Interplanar Spacing d(Å) | Strength |
| 3.15 ± 0.05 | W |
| 2.89 ± 0.05 | M |
| 2.51 ± 0.05 | W |

*VS represents very strong; S strong; M medium strength; and W weak.

A typical synthetic method, of indicating pentasil zeolite is shown, for example, in U.S. Pat. No. 3,702,886 and U.S. Pat. No. 4,511,547.

The pentasil zeolite has a characteristic X-ray diffraction pattern shown in Table 3.

TABLE 3

| X-ray Diffraction Pattern | |
|---|---|
| Interplanar Spacing d(Å) | Strength |
| 11.2 ± 0.2 | S |
| 10.1 ± 0.2 | S |
| 9.8 ± 0.2 | M |
| 6.37 ± 0.1 | W |
| 6.00 ± 0.1 | W |
| 5.71 ± 0.1 | W |
| 5.58 ± 0.1 | W |
| 4.37 ± 0.08 | W |
| 4.27 ± 0.08 | W |
| 3.86 ± 0.08 | VS |
| 3.82 ± 0.08 | VS |
| 3.75 ± 0.08 | S |
| 3.72 ± 0.08 | S |
| 3.66 ± 0.05 | M |
| 3.00 ± 0.05 | M |
| 2.00 ± 0.05 | W |

*VS represents very strong; S strong; M medium strength; and W weak.

Of the foregoing zeolites, the beta zeolite and the mordenite zeolite have the concentration of each of the DCT isomers increased if the concentration is lower.

The pentasil zeolite has pores of smaller diameter and is thus usable for isomerization among 2,5-DCT, 2,4-DCT and 3,4-DCT isomers, but is not usable for isomerization to produce the isomers having greater molecular diameter, namely 2,6-DCT, 3,5-DCT and 2,3-DCT isomers. Thus, the zeolites should be used according to the intended purpose.

From the isomerization capacity and the selectivity of isomerization the mordenite zeolite is most preferably used.

In the isomerization reaction of the present invention, the acid types of zeolites are used. The acid type zeolites are, as well known, obtainable by ion-exchanging cations in the zeolite with the hydrogen ion or with a di- or poly-valent cation. Particularly, the acid type zeolites with the cation being ion-exchanged with the hydrogen ion are preferable, since they are highly active.

For obtaining a zeolite ion-exchanged with hydrogen ion, there is usually employed a method of directly ion-exchanging the zeolite with an aqueous solution of an acid or ion-exchanging the metal cation with the ammonium ion as a hydrogen ion precursor and then calcining. If the zeolite has a cation containing organic nitrogen, the acid type zeolite can be produced by decomposing the cation containing organic nitrogen through calcination and converting it to a hydrogen ion. Of course, it is possible to ion-exchange the alkali metal ions such as sodium present in the zeolite at the time of formation of the zeolite by the ion exchange method stated above.

As a metal component which is another essential component of the catalyst according to the invention, there is used at least one metal selected from the group consisting of rhenium, nickel, and silver. However, other hydrogenation metals such as platinum, molybdenum and cobalt are not preferable.

Rhenium may be present in the form of a metal or a compound such as oxide, sulfide or halide. But, in either case, an amount of rhenium is preferably in the range of from about 0.01 to about 2.0%, more preferably about 0.05 to about 1.0%, by weight expressed as the rhenium atom based on the weight of the entire catalyst. For addition of the rhenium component, the rhenium component may be directly carried in part or whole on the zeolite component, or may be carried in a refractory oxide carrier such as alumina. It is also possible to physically admix the rhenium metal or a rhenium compound such as oxide, sulfide or halide with the zeolite component. Among these methods, it is most preferable to impregnate the zeolite component into an aqueous solution of a water-soluble rhenium compound such as perrhenic acid, ammonium perrhenate or rhenium trichloride.

Nickel or silver may be introduced into the zeolite by the ion-exchange method, or carried in the zeolite by the impregnation method or the kneading method. The amount of nickel is preferably in the range of from about 0.05 to about 5%, more preferably about 0.1 to about 3% by weight expressed as the nickel atom and based on the weight of the entire catalyst. the amount of silver is preferably in the range from about 0.1 to about 15%, more preferably about 0.1 to about 10% by weight, expressed as the silver atom and based on the weight of the entire catalyst.

As the nickel component, a soluble nickel salt such as nickel nitrate or nickel chloride may be preferably used. Nickel may be also used in the form of nickel sulfide obtained by contacting a catalyst containing nickel with hydrogen sulfide. As the silver component, a soluble silver salt such as silver nitrate may be preferably used.

In the invention, such catalyst is normally used in the form of a mold. The molding method is not specially limited, and rolling, extrusion and compression molding are usable. Binders such as alumina sol and clay may be added at the time of molding, if required. Such zeolite mold is dried and subsequently calcined at 300° to 700° C. The foregoing ion-exchange treatment or addition of the metal component, such as rhenium, nickel and silver is preferably made after molding for ease of the preparation of catalyst. The catalyst thus prepared is dried and subsequently calcined at 300° to 700° C. before its use.

Another requirement constituting the process of isomerization of the invention is the presence of hydrogen in the isomerization reaction. A concentration of hydrogen is preferably in the range from 0.003 to 10, more preferably 0.03 to 1 mol/mol, in terms of mol ratio of hydrogen to feed stock (hereinafter referred to as "$H_2/F$").

In the present invention, the isomerization is carried out by contacting a mixture of DCT isomers containing an objective DCT isomer at a low concentration with a catalyst containing an acid type zeolite and at least one component of metal selected from the group consisting of rhenium, nickel and silver in the presence of hydrogen.

The isomerization reaction can be performed according to various known isomerization procedures either in the gas or liquid phase. But, a more preferable procedure is one wherein the isomerization is carried out with DCT maintained in a liquid phase, and with the hydrogen gas at least partially dissolved in the liquid phase DCT. When the high boiling point-product produced on the catalyst reacts in the liquid phase, it flows out of the system together with the liquid DCT. But, in the case of the gas phase, the product remains on the catalyst or in a coke component which tends to damage the catalyst and inhibit its activity.

Any of the fixed bed, moving bed and fluidized bed systems is usable, but the fixed bed flow reaction is particularly preferable from the viewpoint of ease of operation.

The reaction temperature is normally 200° to 500° C., preferably 250° to 450° C. The reaction pressure is not particularly limited, but in the case of the liquid phase reaction, the reaction pressure must of course be set so that the reaction system is maintained in a liquid phase.

The weight hour space velocity (hereinafter referred to as "WHSV") is 0.05 to $10Hr^{-1}$, preferably 0.1 to $5Hr^{-1}$.

The invention will be more clearly understood with reference to the following Examples.

EXAMPLE 1

96.2 g of an aqueous solution of tetraethylammonium hydroxide (content, 20%) and 16.8 g of an aqueous solution of sodium aluminate were dissolved in 254.1 g of water.

To this solution, 52.6 g of silicic acid was added, and the mixture was stirred to provide a slurry of aqueous mixture. The composition in molar ratio was as follows.

| | |
|---|---|
| $SiO_2/Al_2O_3$ | 25 |
| $RN^+/(RN^+ + Na^+)$ | 0.544 |
| $OH^-/SiO_2$ | 0.30 |
| $H_2O/OH^-$ | 80 |

This mixture slurry was charged to an autoclave of 500 ml capacity. After sealing, the heating was made to 160° C. with stirring and crystallization was allowed to take place for 11 days. Thereafter, the product was cooled then filtered and washed with distilled water five times and dried overnight at about 120° C.

The obtained product was determined by the X-ray diffraction, and the X-ray diffraction pattern was substantially the same with that of the beta zeolite shown in Table 1.

EXAMPLE 2

To a powder of the beat zeolite prepared in Example 1, an alumina sol was added by 15 wt % as equivalent to $Al_2O_3$. The mixture was kneaded and then the kneaded mass was extruded through a screen of 1mm $\phi$ and thereafter classified and obtained the molded particle having particle size of 14 to 24 mesh. The molded particles were dried overnight at about 120° C. and calcined at 540° C. for 2 hours in air. Using a 10 wt % aqueous solution of ammonium chloride, this beta zeolite mold was ion-exchanged five times at a solid-liquid ratio of 2.0 liter/kg and at about 90° C. then washed with distilled water thoroughly.

Next, taking an aqueous solution of perrhenic acid in an amount of 0.05 wt % as rhenium metal to the catalyst, the catalyst was impregnated and allowed to stand for 2 hours at room temperature. Thereafter, the solution was drained, and the product was dried overnight at 120° C. then calcined at 540° C. for 2 hours.

This catalyst is called as catalyst "A".

Using the catalyst "A", and a fixed bed flow reactor, the isomerization reaction of DCT was carried out in liquid phase in the presence of hydrogen.

The composition of the reaction feed stock was: 2,5-DCT, 60.4%; 2,6-DCT, 0.93%; 3,5-DCT, 0.00%; 2,4-DCT, 32.9%; 3,4-DCT, 2.13%; and 2,3-DCT, 3,60%.

Reaction Conditions

| | |
|---|---|
| WHSV | $0.60 Hr^{-1}$ |
| Reaction temperature | 300° C. |
| Reaction pressure | 30 $kg/cm^2G$ |
| $H_2/F$ | 0.28 mol/mol |

The result is shown in FIG. 1.

COMPARATIVE EXAMPLE 1

A catalyst was prepared similarly to Example 2, except that no rhenium component was added.

This catalyst is called "B".

The reaction was carried out under the same conditions that those of Example 2 except using the catalyst "B".

The result is shown in FIG. 1.

Comparing Example 2 and Comparative Example 1 with each other in reference to FIG. 1, it will be seen that by the rhenium component, the isomerization activity to 2,6-DCT has been improved along with improvement of the degradation with reaction time of the isomerization activity.

EXAMPLE 3

To a powder of synthetic mordenite zeolite ($SiO_2/Al_2O_3$ ratio, 19.5 mol/mol), an alumina sol was added in an amount of 15 wt % as equivalent to $Al_2O_3$, and after kneading, the kneaded mass was extruded through a screen of 1 mm$\phi$ and thereafter classified and obtained the molded particle having particle size of 14 to 24 mesh. The molded particles were dried overnight at about 120° C. and calcined at 540° C. for 2 hours in air. Then, using a 10 wt % aqueous solution of ammonium chloride, this mordenite zeolite mold was ion-exchanged five times at a solid liquid ratio of 2.0 liter/kg and at about 90° C. and washed with distilled water thoroughly.

Next, taking an aqueous solution of perrhenic acid in an amount of 0.2 wt % as rhenium metal to the catalyst, the catalyst was impregnated and allowed to stand for 2 hours at room temperature. Thereafter, the solution was drained, and the product wa dried overnight at 120° C. then calcined at 540° C. for 2 hours.

This catalyst is called "C".

Using the catalyst "C", the DCT isomerization reaction was carried out in liquid phase under the following reaction conditions.

The result is shown in Table 4.

Reaction Conditions

| | |
|---|---|
| WHSV | $0.60 Hr^{-1}$ |
| Reaction temperature | 330° C. |
| Reaction pressure | 30 $kg/cm^2G$ |
| $H_2/F$ | 0.28 mol/mol |

EXAMPLE 4

The reaction was carried out in a similar manner to Example 3, using the catalyst "C" of Example 3 at a reaction temperature of 350° C.

The result is shown in Table 4.

Figure 2:
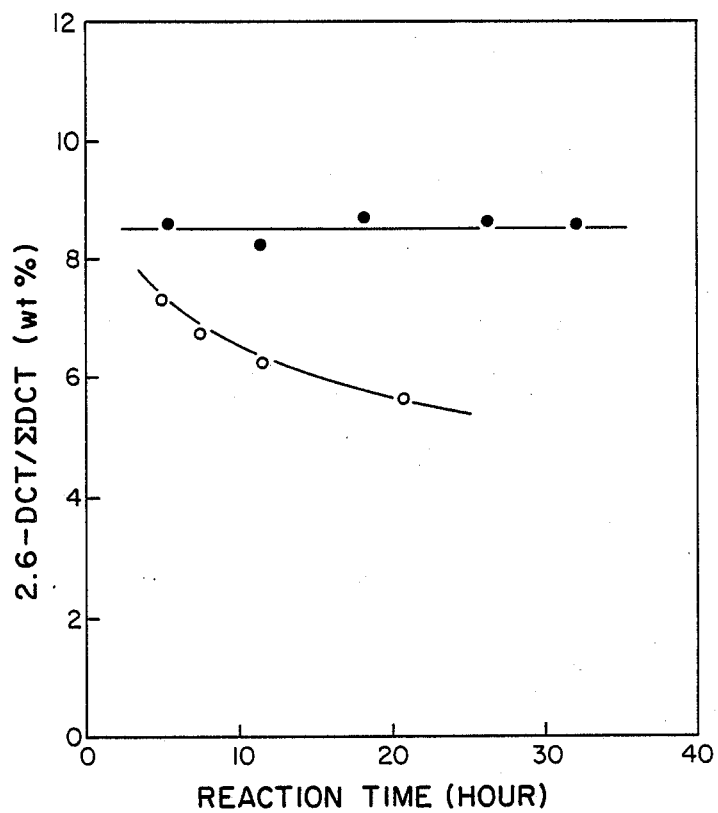
FIG. 2 is a graph showing the relation between the concentration of 2,6-DCT and the reaction time, with respect to the results of Example 4 and Comparative Example 3 of the specification.

The isomerization capacity to 2,6-DCT is shown as a function of the reaction time in FIG. 2. Degradation with reaction time of the catalyst was scarcely noted, and a distinguished isomerization capacity was exhibited.

COMPARATIVE EXAMPLE 2

A catalyst was prepared similarly to Example 3, except that no rhenium component was added. This catalyst is called "D".

Using the catalyst "D", the DCT isomerization reaction was carried out under the same reaction conditions with those of Example 4.

The results is shown in Table 4.

From Table 4, it will be clearly seen that by adding the rhenium component, the concentrations of 2,6-DCT, 3,5-DCT, 3,4-DCT and 2,3-DCT isomers have increased.

COMPARATIVE EXAMPLE 3

The reaction was carried out in a similar manner to Example 4, using the catalyst "D" of Comparative Example 2.

The result is shown in FIG. 2.

It will be seen that in the absence of rhenium, which is a hydrogenation component, the isomerization capacity to 2,6-DCT decreases greatly with the reaction time.

EXAMPLE 5

To a powder of synthetic mordenite zeolite ($SiO_2$/$Al_2O_3$ ratio, 19.5 mol/mol), an alumina sol was added in an amount of 15 wt % as equivalent to $Al_2O_3$, and after kneading, the mixture was molded to 14 to 24 mesh. The molded particles were dried overnight at about 120° C. and calcined at 540° C. for 2 hours in air. Using a 10 wt % aqueous solution of ammonium chloride, this mordenite zeolite mold was ion-exchanged for five times at a solid liquid ratio of 2.0 liter/kg and at about 90° C. then washed with distilled water thoroughly.

Next, taking an aqueous solution of perrhenic acid in an amount of 0.2 wt % as rhenium metal to the catalyst, the catalyst was impregnated and allowed to stand for 2 hours at room temperature. Thereafter, the solution was drained, and the product was dried overnight at about 120° C. then treated at 290° C. for 2 hours in the presence of hydrogen sulfide to transform the rhenium component into rhenium sulfide. The product was then calcined at 540° C. for 2 hours in atmosphere.

This catalyst is called "E".

Using the catalyst "E", the isomerization reaction of DCT was carried out.

The result is shown in Table 4.

COMPARATIVE EXAMPLE 4

A catalyst was prepared similarly to Example 3, except that platinum was used as a hydrogenation component in place of the rhenium.

For the platinum component, an aqueous solution of chloroplatinic acid was used in an amount of 0.005 wt % as platinum metal to the catalyst.

This catalyst is called "F".

Using the catalyst "F", the isomerization reaction of DCT was carride out. The result is shown in Table 4. The isomerization capacity is low, and there are produced many by-products other than DCT.

COMPARATIVE EXAMPLE 5

Similarly to Example 3, a catalyst was prepared, except that molybdenum was used in place of the rhenium as a hydrogenation component.

For the molybdenum component, an aqueous solution of ammonium molybdate was used in an amount of 3 wt % as molybdenum metal to the catalyst. This catalyst is called "G". Using the catalyst "G", the isomerization reaction of DCT was carried out. The result is shown in Table 4. The isomerization capacity is low, and there are produced many by-products other than DCT.

EXAMPLE 6

Similarly to Example 3, a catalyst was prepared, except that nickel was used in place of the rhenium as a hydrogenation component.

For the nickel component, an aqueous solution of nickel nitrate in an amount of 1.0 wt % as nickel metal to the catalyst.

This catalyst is called "H38 .

Using the catalyst "H38 , the isomerization reaction of DCT was carried out.

The results is shown in Table 4.

EXAMPLE 7

To a powder of synthetic morderite zeolite, an alumina sol was added in an amount of 15 wt % as equivalent $Al_2O_3$. After kneading, the mixture was molded to 14 to 24 mesh. The molded particles were dried overnight at about 120° C. and calcined at 540° C. for 2 hours in air. Using a 10 wt % aqueous solution of ammonium chloride, this mordenite zeolite mold was ion-exchanged for five times at a solid-liquid ratio of 2.0 liter/kg and at about 90° C. then washed with distilled water.

Next, taking an aqueous solution of silver nitrate in amount of 2 wt % as silver metal to the catalyst, the catalyst was ion-exchanged at room temperature for 2 hours and then washed with distilled water. The catalyst was dried overnight at about 120° C. and then calciaed at 540° C. for 2 hours.

This catalyst is called "I".

Using the catalyst "I", the isomerization reaction of DCT was carried out.

The results is shown in Table 4.

EXAMPLE 8

A catalyst was prepared similarly to Example 7, except that the catalyst was ion-exchanged with an aqueous solution of silver nitrate in amount of 5 wt % as silver metal to the catalyst.

This catalyst is called "J".

Using this catalyst "J", the isomerization reaction of DCT was carried aut at a reaction temperatwe of 350° C.

Figure 3:
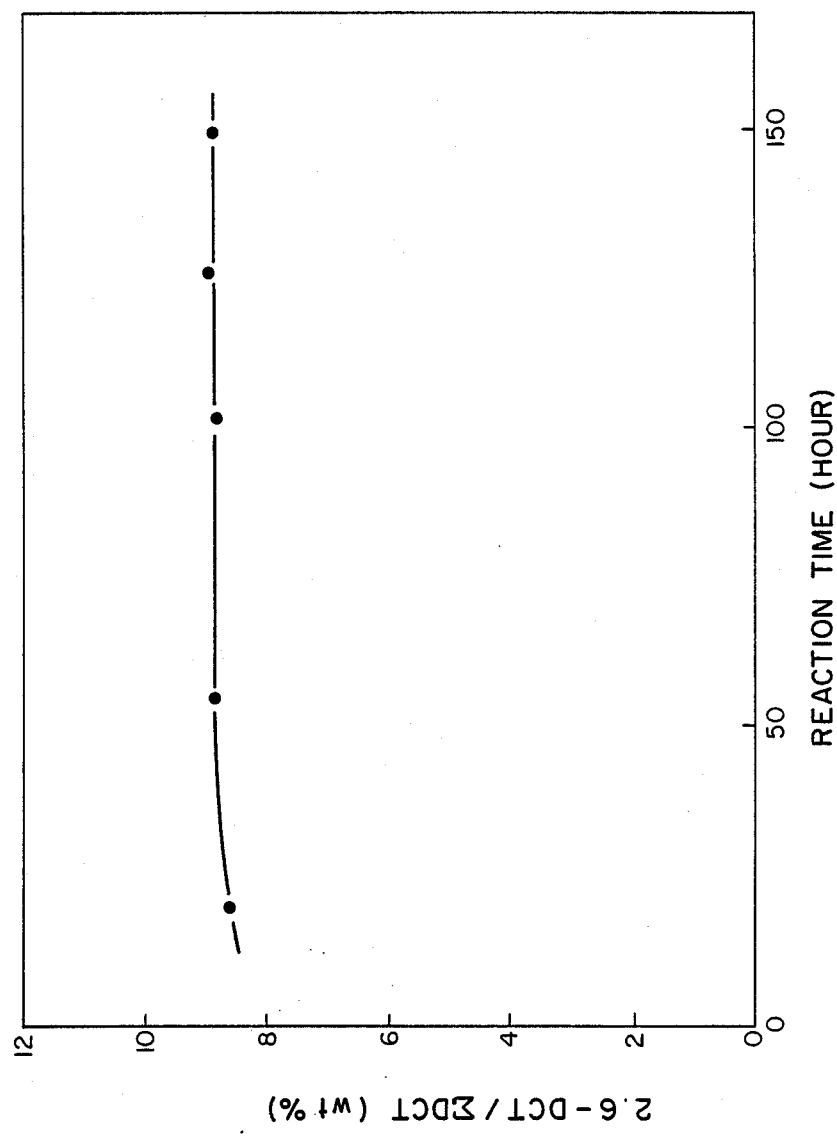
FIG. 3 is a graph showing the relation between the concentration of 2,6-DCT and the reaction time, with respect to the results of Example 8 of the specification.

This result is shown in FIG. 3.

TABLE 4

| Examples<br>Catalysts | | Example 3<br>C | Comparative Example 2<br>D | Example 4<br>C | Example 5<br>E |
|---|---|---|---|---|---|
| Reaction conditions | WHSV (Hr$^{-1}$) | 0.60 | 0.60 | 0.60 | 0.60 |
| | Reaction temperature (°C.) | 330 | 330 | 350 | 330 |
| | Reaction pressure (kg/cm$^2$G) | 30 | 30 | 30 | 30 |
| | H$_2$/F (mol/mol) | 0.28 | 0.28 | 0.28 | 0.28 |
| | Reaction time (Hrs) | 24 | 21 | 18 | 12 |
| | Feed stock | | | | |
| Liquid composition | B, T, X (wt %) | 0.16 | 0.21 | 0.19 | 0.29 | 0.22 |
| | CB | | 0.33 | 0.32 | 0.67 | 0.67 |
| | CT | | 1.23 | 0.50 | 1.61 | 1.15 |
| | DCB | | 0.51 | 0.44 | 0.98 | 1.07 |
| | DCX | | 0.81 | 0.51 | 1.98 | 1.75 |
| | ΣDCT | 99.8 | 96.9 | 98.0 | 94.5 | 95.1 |
| Isomer concentrations | 2.5-DCT (wt %) | 6.04 | 53.1 | 54.6 | 47.4 | 46.7 |
| | 2.6-DCT | 0.93 | 5.42 | 4.57 | 8.59 | 8.99 |
| | 3.5-DCT | 0.00 | 1.14 | 0.92 | 2.60 | 2.73 |
| | 2.4-DCT | 32.9 | 32.5 | 32.5 | 31.9 | 32.0 |
| | 3.4-DCT | 2.13 | 3.19 | 2.92 | 4.15 | 4.15 |
| | 2.3-DCT | 3.60 | 4.64 | 4.48 | 5.31 | 5.44 |

| Examples<br>Catalysts | | Comparative Example 4<br>F | Comparative Example 5<br>G | Example 6<br>H | Example 7<br>I |
|---|---|---|---|---|---|
| Reaction conditions | WHSV (Hr$^{-1}$) | 0.60 | 0.60 | 0.60 | 0.60 |
| | Reaction temperature (°C.) | 330 | 330 | 330 | 350 |
| | Reaction pressure (kg/cm$^2$G) | 30 | 30 | 30 | 30 |
| | H$_2$/F (mol/mol) | 0.28 | 0.28 | 0.06 | 0.06 |
| | Reaction time (Hrs) | 12 | 12 | 21 | 21 |
| | Feed stock | | | | |
| Liquid composition | B, T, X (wt %) | 0.16 | 0.43 | 0.34 | 0.31 | 0.20 |
| | CB | | 0.25 | 0.40 | 0.55 | 0.48 |
| | CT | | 4.76 | 6.44 | 2.59 | 1.47 |
| | DCB | | 0.31 | 1.14 | 0.96 | 0.67 |
| | DCX | | 0.24 | 0.69 | 1.26 | 1.24 |
| | ΣDCT | 99.8 | 94.0 | 91.0 | 94.3 | 95.9 |
| Isomer concentrations | 2.5-DCT (wt %) | 60.4 | 56.4 | 57.7 | 53.1 | 49.2 |
| | 2.6-DCT | 0.93 | 3.09 | 1.95 | 5.17 | 7.29 |
| | 3.5-DCT | 0.00 | 0.63 | 0.37 | 1.22 | 1.94 |
| | 2.4-DCT | 32.9 | 33.0 | 34.1 | 32.8 | 32.3 |
| | 3.4-DCT | 2.13 | 2.68 | 2.21 | 3.12 | 4.00 |
| | 2.3-DCT | 3.60 | 4.23 | 3.62 | 4.63 | 5.20 |

*B, T, X: the total amount of benzene, toluene, and xylene
CB: chlorobenzene
CT: chlorotoluene
DCB: dichlorobenzene
DCX: dichloroxylene
ΣDCT: the total amount of dichlorotoluene isomers

EXAMPLE 9

9.22 grams of solid caustic soda and 12.5 grams of tartaric acid were dissolved in 344.2 grams of water. To this solution, 17.5 grams of a sodium aluminate solution was added into a homogeneous solution. To this mixed solution, 66.0 grams of silicic acid was added gradually with stirring, and thus an aqueous reaction mixture in the form of a uniform slurry was prepared. The composition (molar ratio) of this reaction mixture was as follows.

| | | |
|---|---|---|
| SiO$_2$/Al$_2$O$_3$ | 30 | |
| H$_2$O/SiO$_2$ | 20 | |
| OH$^-$/SiO$_2$ | 0.17 | |
| A/Al$_2$O$_3$ | 25 | A: Tartarate |

This mixture was charged to an autoclave of a capacity of 500 ml which was then closed. The mixture was then heated at 160° C. for 72 hours with stirring for crystallization. Thereafter, the product was cooled, filtered, washed and distilled water five times and dried overnight at about 120° C.

The obtained product was determined by the X-ray diffraction. As the result, the X-ray diffraction pattern was substantially the same with that of the pentasil zeolite shown in Table 3.

EXAMPLE 10

To a powder of the pentasil zeolite prepared in Example 9, an alumina sol was added in an amount of 15 wt % as equivalent to $Al_2O_3$, and after kneading, the mixture was molded to 14 to 24 mesh. The molded particles were dried overnight at about 120° C. and calcined at 540° C. for 2 hours in air.

Using a 10 wt % aqueous solution of ammonium chloride, the pentasil zeolite mold was ion-exchanged five times at a solid liquid ratio of 2.0 liter/kg and at about 90° C. and washed with distilled water thoroughly. Next, taking an aqueous solution of ammonium perrhenate in an amount of 0.2 wt % as rhenium metal to the catalyst, the catalyst was impregnated and allowed to stand for 2 hours at room temperature. Thereafter, the solution was drained, and the product was dried overnight at about 120° C. and calcined at 540° C. for 2 hours.

This catalyst is called the catalyst 37 K38 .

Using the catalyst "K" the isomerization reaction of 2,4-DCT was carried out in liquid phase in the presence of hydrogen. The results is shown in Table 5. Isomerization from 2,4-DCT to 2,5-DCT and 3,4-DCT is noted, but isomerization to 2,6-DCT, 3,5-DCT and 2,3-DCT is not noted. It would be considered that 2,6-DCT, 3,5-DCT and 2,3-DCT of greater molecular size were not produced with the pentasil type zeolite of smaller pore diameter.

COMPARATIVE EXAMPLE 6

Similarly to Example 10, a catalyst was prepared, provided rhenium or the hydrogenation component was not added.

This catalyst is called the catalyst "L".

Using the catalyst "L", the isomerization reaction of 2,3-DCT was carried out in liquid phase in a system in which hydrogen was not present. The result is shown in Table 5. The lower 2,4-DCT isomerization activity is considered to be due to degradation with time of the catalyst.

EXAMPLE 11

Using the catalyst "A" prepared in Example 2, the isomerization reaction of 2,4-DCT was carried out in liquid phase in the presence of hydrogen. The result is shown in Table 5.

Isomerization from 2,4-DCT to all of the other isomers will be noted.

COMPARATIVE EXAMPLE 7

Using the catalyst "A" prepared in Example 2, isomerization of 2,4-DCT was carried out in liquid phase in a system in which hydrogen is not present. The result is shown in Table 5.

TABLE 5

| | Examples<br>Catalysts | | Example 10<br>K | Comparative Example 6<br>L | Example 11<br>A | Comparative Example 7<br>A |
|---|---|---|---|---|---|---|
| Reaction conditions | WHSV ($Hr^{-1}$) | | 0.40 | 0.40 | 0.60 | 0.60 |
| | Reaction temperature (°C.) | | 310 | 310 | 300 | 300 |
| | Reaction pressure (kg/cm²G) | | 30 | 30 | 30 | 30 |
| | $H_2$/F (mol/mol) | | 0.06 | 0.00 | 0.06 | 0.00 |
| | Reaction time (Hrs) | | 24 | 24 | 24 | 24 |
| | | Feed stock | | | | |
| Isomer concentrations | 2,5-DCT (wt %) | 0.60 | 20.1 | 4.71 | 29.2 | 10.8 |
| | 2,6-DCT | 0.05 | 0.00 | 0.00 | 2.57 | 0.49 |
| | 3,5-DCT | 0.00 | 0.00 | 0.00 | 3.91 | 1.36 |
| | 2,4-DCT | 99.4 | 75.4 | 94.3 | 57.1 | 83.9 |
| | 3,4-DCT | 0.00 | 4.44 | 1.00 | 2.36 | 1.10 |
| | 2,3-DCT | 0.00 | 0.00 | 0.00 | 4.77 | 2.40 |

What is claimed is:

1. A process for the isomerization of dichlorotoluene comprising the steps of contacting a mixture of isomers of dichlorotoluene with a catalyst containing an acid type zeolite selected from the group consisting of mordenite zeolite and beta zeolite and at least one component of metal selected from the group consisting of rhenium, nickel, and silver, said isomerization being conducted in the presence of hydrogen.

2. A process according to claim 1, wherein said metal is rhenium.

3. A process according to claim 1, wherein said metal is silver.

4. A process according to claim 1, wherein the isomerized dichlorotoluene contains 2,6-dichlorotoluene.

5. A process according to claim 1, wherein said catalyst contains rhenium in an amount of 0.001 to 2.0 percent by weight.

6. A process according to claim 1, wherein said catalyst contains silver in an amount of 0.1 to 15 percent by weight.

7. A process according to claim 1, wherein hydrogen is presented in the range of 0.03 to 10 mol/mol. in terms of mol ratio of hydrogens to the feed stock.

* * * * *